United States Patent [19]

Mahoney, III et al.

[11] Patent Number: 5,413,306
[45] Date of Patent: May 9, 1995

[54] TEST FRAME

[75] Inventors: Richard J. Mahoney, III, Mansfield; Paulo A. Martin, Fall River, both of Mass.; Graham E. Mead, Buckinghamshire, England; David W. Scanlon, Rehoboth, Mass.

[73] Assignee: Instron Corporation, Canton, Mass.

[21] Appl. No.: 27,709

[22] Filed: Mar. 5, 1993

[51] Int. Cl.⁶ .................. F16M 11/00; G01N 3/02
[52] U.S. Cl. .................... 248/676; 248/127
[58] Field of Search ............... 248/125, 176, 676, 678, 248/127, 146

[56] References Cited

U.S. PATENT DOCUMENTS

| | | | |
|---|---|---|---|
| 3,462,110 | 8/1969 | Cheslock | 248/125 X |
| 4,508,302 | 4/1985 | Hausser | 248/125 X |
| 4,537,082 | 8/1985 | Meline et al. | |
| 4,754,942 | 7/1988 | Berg et al. | 248/176 X |
| 5,110,076 | 5/1992 | Snyder et al. | 248/125 |
| 5,188,323 | 2/1993 | David | 248/125 X |

FOREIGN PATENT DOCUMENTS

| | | |
|---|---|---|
| 0507514 | 10/1992 | European Pat. Off. . |
| 2620323 | 3/1989 | France ................... 248/176 |
| 0601741 | 5/1948 | United Kingdom . |
| 1073219 | 6/1967 | United Kingdom . |
| 9102233 | 2/1991 | WIPO . |

Primary Examiner—Ramon O. Ramirez

[57] ABSTRACT

A testing machine frame is provided with facing extruded column covers extending between a base and a top housing, the columns continuous cross-sections providing a partially enclosed vertical zone with a vertical opening, the opening being closed above and below a crosshead with accordion blinds, and T-slots for carrying crosshead limit stops and accessories.

10 Claims, 4 Drawing Sheets

TEST FRAME

FIELD OF THE INVENTION

This invention relates to test frames, and more particularly to materials testing machines embodying such frames.

1. Background of the Invention

It is known in the art to enclose drive screws and guide rods, either by a combination of sheet metal and accordion blinds, or by a full enclosure therearound by accordion blinds.

2. Summary of the Invention

Improved devices for imposing stress may be provided by using extruded members to partially enclose stressing members movable relative to the extruded members.

In preferred embodiments, there are provided a pair of extruded aluminum members open at transversely facing sides, with a stressing member extending through the opening in each extruded member and being mounted on drive screws and guide rods for movement driven by the former and guided by the latter, one such drive screw and one such guide rod extending within each of the extruded members and being enclosed by an extruded member in cooperation with an accordion blind, the extruded members being provided with T-slots for selectively mounting therein T-slides.

Preferred Embodiment

Description of the preferred embodiment, in structure and operation, follows.

Drawings

Structure

Figure 1:
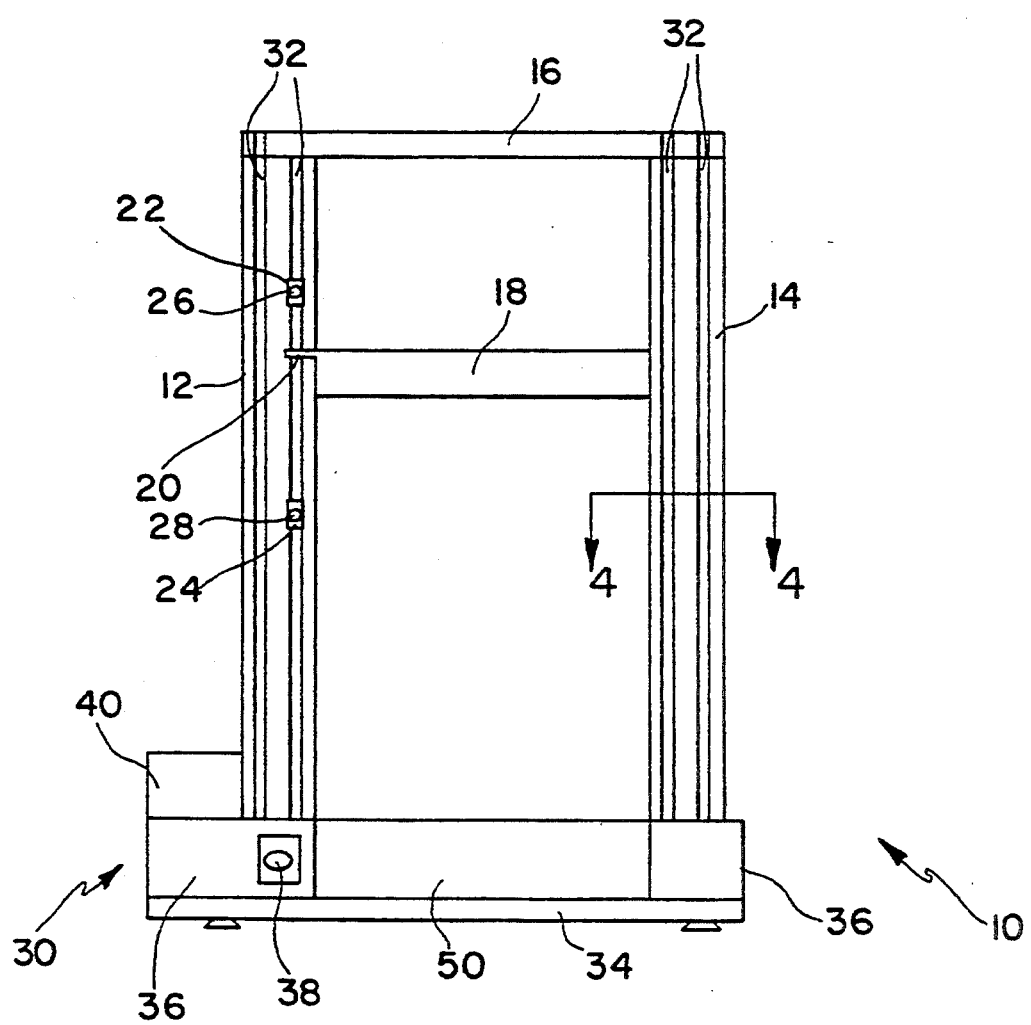
FIG. 1 is a front elevation view, somewhat simplified, of the preferred embodiment.
Figure 2:
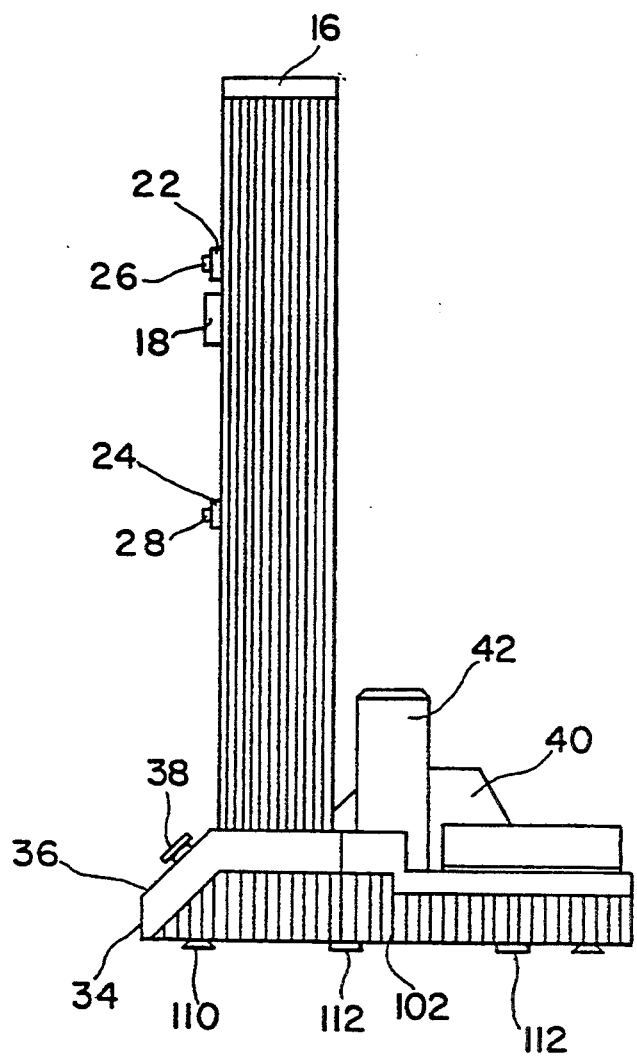
FIG. 2 is a side elevation view, again somewhat simplified, thereof.

Turning now to FIG. 1, there is shown a materials testing machine frame indicated generally at 10. It includes two extruded aluminum cover columns 12, 14, a top housing 16, a crosshead 18 with protruding finger 20, movable limit stops 22, 24, with respectively cooperating knobs 26, 28, a base housing indicated generally at 30, two slots 32 in each column, cooperating with slots in top housing 16 to provide therewith three continuous slots from base housing 30 to the top of top housing 16, and a fourth along column 12.

Base housing 30 includes front lower portion 34 and front upper portion 36, integrally injection molded in a single plastic molding. Extending from upper portion 36 is control knob 38, and mounted on upper portion 36 are electronics components housing 40 and motor housing 42.

Interposed between coplanar surfaces 36 is a curved surface 50 defined by moving a vertical line along an arc of a circle of large radius; curved surface 50 intersects a horizontal planar surface of lower portion 34 to provide a shelf.

Figure 4:
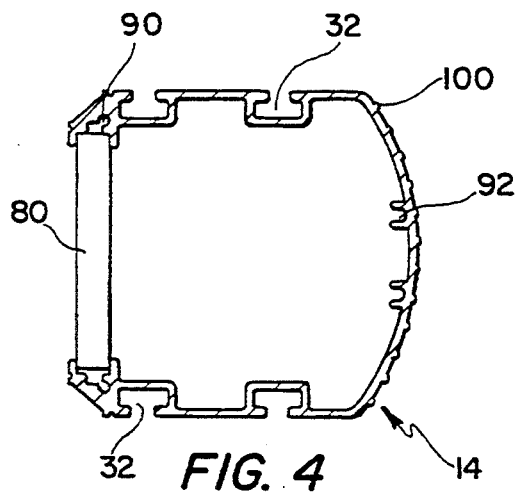
FIG. 4 is a sectional view, taken at 4—4 of FIG. 1 and enlarged.
Figure 6:
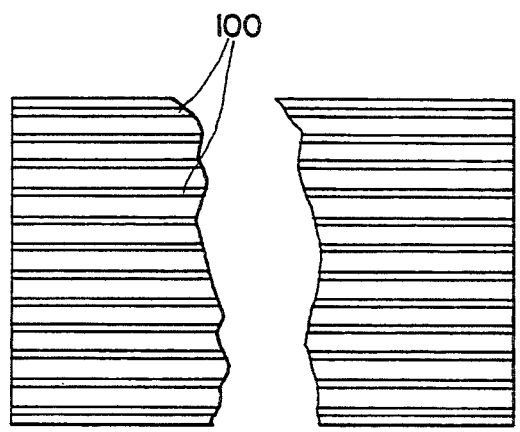
FIG. 6 is a side elevation view corresponding otherwise to the view of FIG. 5.
Figure 5:
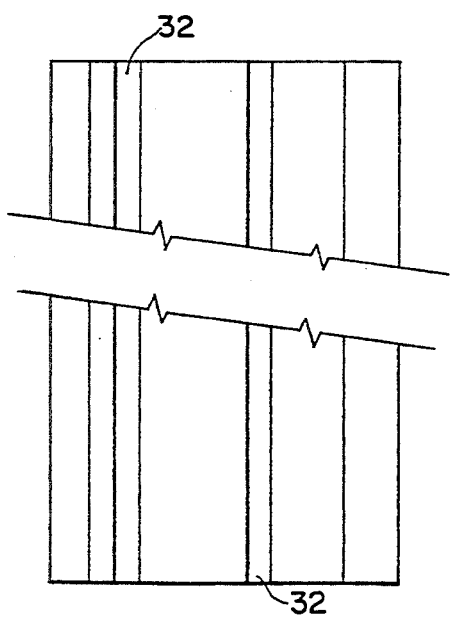
FIG. 5 is an end elevation view of the column show in cross-section in FIG. 4, and to the same scale as FIG. 4.

Column 14 is shown in more detail in FIG. 4.

As here seen, the slots 32 are T-shaped in cross-section.

Figure 3A:
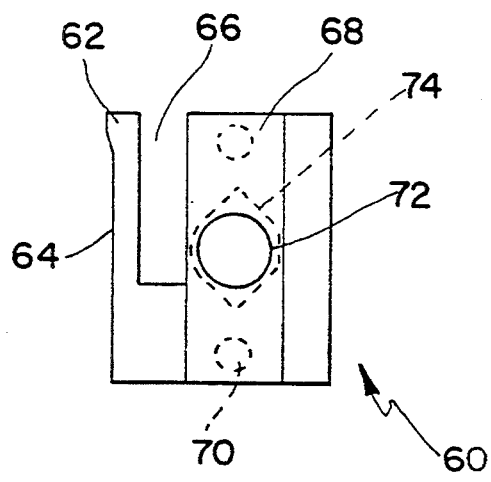
FIG. 3a, 3b, 3c are respectively a front elevation, side elevation, and plan view of a T-slide element of said embodiment.
Figure 3B:
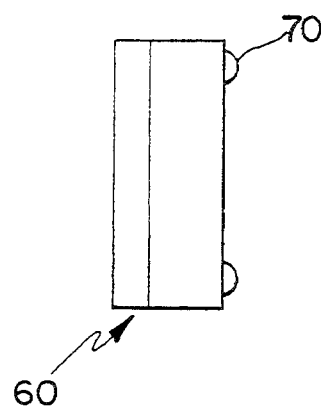
Figure 3C:
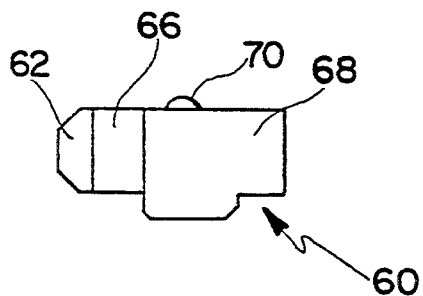

Slides 60, as shown in FIGS. 3a, 3b, and 3c, may be used in slots 32, in which they slidably fit. They may be introduced through the tops of the columns 12, 14 as desired. Bump 62 on springy arm 64 separated by slot 66 from body portion 68 is by arm 64 urged against a slot 32 with enough force to sustain a vertical position in the column or cover. Bumps 70 in cooperation with the aluminum of the cover helps with this function in the perpendicular direction. Hole 72 permits a fastener (not shown) with its head in hexagonal countersink 74 to engage, for example, an accessory desired to be carried in a slot 32. Element 60 is a unitary molding of glass-reinforced polycarbonate plastic.

Similar T-slides 22, 24, provided with vertical holes fixedly carrying rods extending down to limit switches in base 30, cooperate with feeler 20 carried by crosshead 18 to cause vertical movement up or down of crosshead 18 to stop as feeler 20 engages a T-slide 22 or 24.

A guide rod (not shown) for crosshead 18 extends vertically from within base cover 30 to within top housing 16 in each cover 12, 14. Also extending vertically for the same extent, also within the housing 16, is a drive screw (also not shown) mounted to cooperate with crosshead 18 to drive it up and down.

As shown in FIG. 4, an accordion blind 80 is secured, by loop and hook fasteners as the one sold under the Trademark Velcro (not shown), to crosshead 18 at each end on the cross-head top, and at each end on the cross-head bottom, opposing ends being secured by hook and loop fasteners (not shown) to, respectively, the bottom of top member 16 and the top of housing 30. The guide rods and drive screws are thus fully enclosed, the accordion blinds (formed of nylon cloth with a rubbery impregnant) being adapted to open and close as needed.

The extrusions 12, 14 include circular portions 90, 92 to cooperate with pins in top portion 16 in assembling and retaining the latter. A groove provides for adhering therein a scale with linear measurement indicia, and another groove provides for snapping thereinto a slidable indicator of position on the scale.

Elongated bumps 100, are provided to enhance ornamental appearance, molded into the respective parts.

On the bottom of the embodiment are rubber feet 110 and ribs (of strong metal, U-shaped in cross-section) 112, secured on a bottom metal plate (not shown).

Operation

In operation, the invention provides many advantages.

The accordion blinds jointly with the extruded column covers provide complete enclosure of drive screws and guide rods.

Various mountings may be made on T-slides in T-slots. For example, testing accessories such as frame lights and protection shields may be so mounted. Or, relief points for accessory cables may be so provided.

The invention provides not only the above advantages, but is less expensive than the sheet metal cover devices above described, in part because of the integral nature of accordion blind guides and the accessory attachment means, in part because anodizing makes possible eliminating painting, and because of the construction generally.

It makes possible too improved esthetic qualities.

Other Embodiments

Other embodiments will occur to those skilled in the art. For example, other features may be extruded into the columns covers, for example a crosshead guide surface, to enable elimination of guide rods. The material used for the column extrusion may be a metal other than aluminum or plastic.

What is claimed is:

1. A materials testing machine comprising
   a base,
   a top housing vertically spaced therefrom and extending parallel thereto,
   a first column and a second column,
   said first column being horizontally spaced from said second column and extending from said base to said top housing,
   said second column extending also from said base to said top housing,
   each said column including an enclosure wall shaped to provide a partial enclosure of a vertical zone and a vertical opening from said zone,
   said vertical opening of said first column facing said vertical opening of said second column,
   each said column having throughout said column the same extruded cross-sectional configuration.

2. The machine of claim 1 in which said cross-section is identical in said first column and in said second column.

3. The machine of claim 2 includes between said base and said top housing a cross-head generally parallel with said base and said top housing and mounted for selective vertical movement therebetween and which has mounted between said crosshead and base and said top housing four accordion blinds, said accordion blinds being mounted over each said vertical opening above and below said crosshead.

4. The machine of claim 1 in which said each column includes interiorly thereof an extruded accordion blind guide.

5. The machine of claim 1 in which said each column includes mounting slots.

6. The machine of claim 5 in which said each slots are T-shaped in cross-section, the non-crossing part of the T extending through a surface of said each column.

7. The machine of claim 6 which includes also a T-slide mounted to run in one of said slots.

8. The machine of claim 7 in which said T-slide includes means biasing said T-slide against said one.

9. The machine of claim 1 in which each said column is of aluminum.

10. The machine of claim 5 in which one of said slots carries therein a selectively movable crosshead limit stop.

* * * * *